US008153382B2

(12) United States Patent
Chtourou et al.

(10) Patent No.: US 8,153,382 B2
(45) Date of Patent: Apr. 10, 2012

(54) IMMUNOGLOBULIN G (IGG) CONCENTRATE DEPLETED OF ANTI-A AND ANTI-B ANTIBODIES AND OF POLYREACTIVE IGGS

(75) Inventors: Abdessatar Chtourou, Elancourt (FR); Frederic Dhainaut, Boissy-le-Seo (FR); Philippe Paolantonacci, Gif sur Yvette (FR)

(73) Assignee: Laboratoire Francais du Fractionnement et des Biotechnologies Societe Anonyme, Les Ulis (FR)

( * ) Notice: Subject to any disclaimer, the term of this patent is extended or adjusted under 35 U.S.C. 154(b) by 577 days.

(21) Appl. No.: 12/159,199

(22) PCT Filed: Dec. 26, 2006

(86) PCT No.: PCT/FR2006/002889
§ 371 (c)(1),
(2), (4) Date: Nov. 5, 2008

(87) PCT Pub. No.: WO2007/077365
PCT Pub. Date: Jul. 12, 2007

(65) Prior Publication Data
US 2009/0074749 A1    Mar. 19, 2009

(30) Foreign Application Priority Data

Dec. 26, 2005 (FR) ..................................... 05 13311

(51) Int. Cl.
*G01N 33/53* (2006.01)
(52) U.S. Cl. ......................................... 435/7.1; 436/518
(58) Field of Classification Search .................. None
See application file for complete search history.

(56) References Cited

U.S. PATENT DOCUMENTS

| 4,764,369 | A | 8/1988 | Neurath et al. | |
| 7,186,410 | B2 * | 3/2007 | Chtourou et al. | 424/176.1 |
| 7,744,883 | B2 * | 6/2010 | Bristow | 424/140.1 |

FOREIGN PATENT DOCUMENTS

| EP | 0703922 | 4/1996 |
| EP | 1059088 | 12/2000 |
| FR | 2824568 | 11/2002 |
| WO | WO 94/29334 | 12/1994 |
| WO | WO 98/21593 | 5/1998 |
| WO | WO 99/64462 | 12/1999 |
| WO | WO 01/27623 | 4/2001 |
| WO | WO 02/092632 | 11/2002 |
| WO | WO 2004/091656 | 10/2004 |

OTHER PUBLICATIONS

Huang (Transfusion 2003 vol. 43, p. 758-764).*
Hout et al. (ASAIO Journal vol. 46, p. 702-706), year 2000.*
Cohn et al, 1946 J Am Chem Soc 68,459.
Oncley JL, Melin M, et al The separation of the antibodies, isoagglutinins, prothrombin, plasminogen and bete1-lipoprotein into subtractions of human plasma. >> J Am Chem Soc. Feb. 1949;71(2):541-50.
Bleaker WK, Teeling JL, Verhoeven AJ, Rigter GM, Agterberg J, Tool AT, Koenderman AH, Kuijpers TW, Hack CE. "Vasoactive side effects of intravenous immunoglobulin preparations in a rat model and their treatment with recombinant platelet-activating factor acetylhydrolase." Blood. Mar. 1, 2000;95(5):1856-61.
Steinbuch M, Audran R. "Isolation of IgG immunoglobulin from human plasma using caprylic acid" Rev Fr Etud Clin Biol. Dec. 1969;14(10):1054-8.
Buchta C, Macher M, Höcker P "Potential approaches to prevent uncommon hemolytic side effects of AB0 antibodies in plasma derivatives." Biologicals. Mar. 2005,33(1):41-8.
Wilson JR, Bhoopalam H, Fisher M. "Hemolytic anemia associated with intravenous immunoglobulin." Muscle Nerve. Sep. 1997;20(9):1142-5.
Copelan EA, Strohm PL, Kennedy MS, Tutschka PJ. "Hemolysis following intravenous immune globulin therapy." Transfusion. Sep.-Oct. 1986:26(5):410-2.
Misbah SA, Chapel HM. "Adverse effects of intravenous immunoglobulin" Drug Saf Oct. 1993;9(4):254-62.
Pharmacopée européenne 2.6.20, 1997.
Mazid MA, Kaplan M. "An improved affinity support and immunoadsorbent with a synthetic blood group oligosaccharide and polymer coating for hemoperfusion." J Appl Biomater. 1992 Spring;3(1):9-15.
Hout MS, LeJeune KE, Schaack TM, Bristow DK, Federspiel WJ. "Specific removal of anti-A and anti-B antibodies by using modified dialysis filters." ASAIO J. Nov.-Dec. 2000;46(6):702-6.
Kazatchkine MD, Dietrich G, Hurez V, Ronda N, Bellon B, Rossi F, Kaveri SV. "V region-mediated selection of autoreactive repertoires by intravenous immunoglobulin (i.v.lg)." Immunol Rev. Jun. 1994;139:79-107.
Coutinho A, Kazatchkine MD, Avrameas S. "Natural autoantibodies." Curr Opin Immunol. Dec. 1995;7(6):812-8.
Berneman A, Ternynck T, Avrameas S. "Natural mouse IgG reacts with self antigens including molecules involved in the immune response." Eur J Immunol. Mar. 1992;22(3):625-33.
Lacroix-Desmazes S, Kaveri SV, Mouthon L, Ayouba A, Malanchere E, Coutinho A, Kazatchkine MD. "Self-reactive antibodies (natural autoantibodies) in healthy individuals." J Immunol Methods. Jul. 1, 1998;216(1-2):117-37.
Bouvet JP, Stahl D, Rose S, Quan CP, Kazatchkine MD, Kaveri SV. "Induction of natural autoantibody activity following treatment of human immunoglobulin with dissociating agents." J Autoimmun. Mar. 2001:16(2):163-72.
Teeling JL, Jansen-Hendriks T, Kuijpers TW, de Haas M, van de Winkel JG, Hack CE, Sleeker WK. "Therapeutic efficacy of intravenous immunoglobulin preparations depends on the immunoglobulin G dimers: studies in experimental immune thrombocytopenia." Blood. Aug. 15, 2001;98(4)1095-9.

(Continued)

*Primary Examiner* — Jacob Cheu
(74) *Attorney, Agent, or Firm* — Juan J. Lizarraga

(57) ABSTRACT

The present invention relates to an immunoglobulin G concentrate for therapeutic use, in which the respective contents of anti-A and anti-B antibodies are in accordance with a negative result in the in vitro indirect Coombs test. This IgG concentrate also has a polyreactive IgG content of between 0.01% and 0.1%, in particular between 0.07% and 0.1%, relative to the total content of IgG.

12 Claims, No Drawings

OTHER PUBLICATIONS

Knezevic-Maramica I, et al "Intravenous immune globulins: an update for clinicians" Transfusion 2003, vol. 43, n°10, pp. 1460-1480.

Nicholls MD, Cummins JC, Davies VJ, Greenwood JK. "Haemolysis induced by intravenously-administered immunoglobulin." Med J Aust. Apr. 3, 1989:150(7):404-6.

Wang Z, Shi J, Zhou Y, Ruan C. "Detection of red blood cell-bound immunoglobulin G by flow cytometry and its application in the diagnosis of autoimmune hemolytic anemia." Int J Hematol. Feb. 2001;73(2):188-93.

Chaudhary R, Das SS, Gupta R, Khetan D. "Application of flow cytometry in detection of red-cell-bound IgG in Coombs-negative AIHA." Hematology. Aug. 2006;11(4):295-300.

Shnaider A, Basok A, Rogachev BV, Ziotnik M, Tomer A. "Severe Coombs'-negative autoimmune hemolytic anemia in a kidney transplant patient" Am J Nephrol. Nov.-Dec. 2001;21(6):494-7.

Gordon JM, Cohen P, Finlayson JS. "Levels of anti-A and anti-B in commercial immune globulins". Transfusion. Jan.-Feb. 1980;20(1):90-2.

Issitt PD "The antiglobulin (Coombs) test, complement in antigen-antibody reactions and in the antiglobulin test, in vivo destruction of incompatible red cells, the alternative pathway of complement, some biological consequences of complement activation in man" Applied Blood Group Serology, Montgomery scientific publications, Miami, FL, US, 1985, pp. 72-115.

* cited by examiner

IMMUNOGLOBULIN G (IGG) CONCENTRATE DEPLETED OF ANTI-A AND ANTI-B ANTIBODIES AND OF POLYREACTIVE IGGS

The present invention relates to an immunoglobulin G concentrate (IgG) depleted of anti-A (AcaA) and anti-B (AcaB) antibodies and having strongly reduced polyreactivity, and to a method to obtain said concentrates.

The use of fractions of human plasma enriched in immunoglobulins (Ig) for the treatment of various infections or congenital deficiencies has been known since the development of Cohn's ethanol precipitation method (Cohn et al, 1946, J. Am. Chem. Soc. 68, 459; Oncley et al, 1949, J. Am Chem. Soc. 71, 541).

There is an increasing need to produce highly purified Ig concentrates, for injection via intravenous route (IgIV), obtained from human plasmas for example. The complex structure of immunoglobulins (four polypeptide chains joined by disulfide bridges), and the variety of antibodies present in the plasma mixture from several thousand donors, are currently factors which do not promote the biotechnological development of immunoglobulins. Although monoclonal antibodies are produced by genetic engineering, their extreme specificity amounts to a disadvantage for therapeutic applications in which polyspecificity appears to be a necessity.

Additionally, numerous pathologies, of autoimmune origin for example, are currently treated with IgG concentrates which has led to a shortage thereof in Europe and the United States in recent years.

Methods to obtain immunoglobulins and in particular IgG concentrates, in addition to selective precipitation of the proteins by ethanol, may also comprise various other treatments such as precipitation by polyethylene glycol, controlled proteolytic enzyme treatment... intended to remove aggregates of immunoglobulin polymers which may activate the complement system with associated risks of anaphylactic reactions. Also, the presence of dimers in IgGIVs has been correlated with arterial tension drops in vivo (Bleeker W. K. et al, Blood, 95, 2000, p. 1856-1861).

An alternative route to ethanol precipitation has been described by Steinbuch et al (Rev. Franç. Et. Clin. et Biol. 1969, XIV, 1054) which has recourse to precipitation by octanoic acid. This acid precipitates most plasma proteins and leaves the immunoglobulins in the supernatant. Purification of these immunoglobulins is obtained by passing through an anion exchanger, DEAE-cellulose, under conditions which do not retain the IgGs. The fraction of non-retained IgG is then concentrated.

Various methods have also been developed to increase the purity of the products using chromatographic techniques. Particular mention may be made of patent applications EP 0 703 922 and WO 99/64462, which describe the association of at least two successive chromatographic steps, one by anion exchange, the other by cation exchange. The specificity of these methods is provided by the property of the anion exchangers whereby they do not retain immunoglobulins G, under conventional chromatography conditions, but instead they fix most of the other proteins co-purified during the pre-purification steps. Similarly patent application WO 02/092632 can be cited, filed by the Applicant, which discloses the preparation of Ig concentrates using a single chromatography step on anion exchanger, conducted at alkaline pH, for their retention on the chromatographic medium.

However, numerous scientific publications indicate that the injection of IgGs obtained by the above fractionating techniques can cause, sometimes severe, accidental haemolysis in patients undergoing treatment. As examples, the following publications can be cited: Buchta C et al, Biologicals, 33, 2005, 41-48, Wilson J. R. et al, Muscle & Nerve, 29(9), 1997, 1142-1145, Copelan E. A. et al, Transfusion, 26, 1986, 410-412 and Misbah S. A. et al, Drug Safety, 9, 1993, 254-262. The study of effects on the blood of patients with haemolysis, performed using the direct Coombs test (direct Coombs test—DCT) in particular, has shown that the red blood cells are coated with immunoglobulins directed against antigens A, B or D present on their surface, thereby causing their haemolysis. This is why the IgGs available on the market are obtained from selected plasmas to avoid the presence of anti-D immunoglobulins or other antibodies high in anti-A or anti-B titres.

Buchta et al, cited above, considered different approaches to achieve a signification reduction in anti-A antibodies, originating from B and O blood group donors, and in anti-B antibodies derived from A and 0-group donors, in plasma derivatives such as IgGs, with a view to minimizing the risks of haemolysis that are directly correlated with the levels of these antibodies, when treating patients with these plasma derivatives. It was notably envisaged to choose the donors, to remove the anti-A and anti-B antibodies, to produce derivatives of blood plasma originating from a specific group, group A and/or B, and to exclude from batches those plasmas having a high titre in anti-A and anti-B antibodies. Some approaches are considered to be non-realistic on account of the cost or complexity of the steps to be taken. It is noted that anti-A and anti-B antibodies are partly removed during the ethanol fractionation mentioned above.

Since the needs for IgGs are constantly increasing, there is a need for increasingly larger pools of donors which, statistically, will include greater numbers of O-group donors. As a result, blood derivatives such as IgGs will contain quantities of anti-A and anti-B antibodies that are too high for their removal by conventional fractionation.

These increasing needs prevent contemplating the possible selection of group AB donors only, in order to ensure a low content of anti-A and anti-B antibodies.

Each batch of purified IgG concentrates or preparations is controlled for anti-A and anti-B antibodies using test 2.6.20 of the European Pharmacopeia (1997) which is an in vitro application of the indirect Coombs test (indirect Coombs test—ICT). The ICT test consists of adding to a suspension of red blood cells, coated with anti-A or anti-B antibodies of IgG type contained in the IgG concentrates, a solution of antibodies (antiglobulins) directed against motifs of human IgG. These antibodies bind to anti-A or anti-B antibodies attached to the red blood cells and thereby cause their agglutination through the formation of bridges between the IgGs. The assay for detection of anti-A or anti-B antibodies is directly inspired by this conventional test in haematological serology (Coombs test).

According to the European Pharmacopeia, IgIVs must not show any agglutination of A or B red blood cells under the ICT test at a dilution of 1:64, conducted with an IgG solution whose initial concentration is reduced to 30 g/l.

This is why IgG samples to be tested must be diluted to obtain a titre i.e. the value of the last dilution which no longer causes agglutination. Negative ICT results on IgIV solutions whose dilutions are lower than the 1:64 dilution, following the European pharmacopeia, indicate a low content of anti-A and anti-B antibodies which is acceptable. However, even with IgG concentrates giving a negative result for the test prescribed by the European pharmacopeia, i.e. those with a dilution ratio of less than 1:64, the risks of haemolytic reactions cannot be excluded (Buchta et al, cited above).

It is to be noted that the American and Japanese pharmacopoeias make no provision for the need to control residual contents of anti-A and anti-B antibodies.

As mentioned above, anti-A and anti-B antibodies are partly removed during the preparation of IgG concentrates by ethanol fractionation, however a residual content is observed which may exceed the upper limit of the European pharmacopeia. Additionally, concentrates prepared following the method developed by the Applicant and described in its patent application WO 02/092632 have a higher content thereof than those obtained by ethanol fractionation. Additional purification of the IgG concentrates thus obtained, with respect to anti-A anti-B antibodies, is therefore necessary since some batches of IgG concentrates may have contents thereof that are higher than the threshold set by the European Pharmacopeia.

One technique to remove these antibodies from IgG concentrates consists of purification by affinity chromatography using immunoadsorbants as medium, of oligosaccharide type similar to antigens A and B of the blood groups, said oligosaccharides particularly being trisaccharides grafted on a chromatographic matrix.

As example, mention may be made of the publication by Mazid M. A. et al, J. Appl. Biomater., 3(1), 1992, 9-15, which uses a chromatographic medium containing silica particles on which are grafted haptenes of synthesized oligosaccharides, characteristic of blood groups A and B, and in particular A-trisaccharides. Also, Hout M. S. et al (ASAIO J, 46(6), 2000, 702-706) describe the use of tubular fibrous membranes grafted with specific anti-A and anti-B antigens for the removal of anti-A and anti-B antibodies from whole blood. It is also reported that said chromatographic mediums are very stable, which limits release of these residual haptenes in the concentrates of interest.

Patent application WO 01/27623 describes a method to obtain a plasma de-specified in antibodies of blood groups A and B i.e. a plasma suitable for any receiver. These specificities are essentially carried by immunoglobulins M (IgM). De-specification is obtained by passing through an experimental affinity medium for group A, then through another affinity medium, also experimental, for group B. In the event of simultaneous presence of anti-A and anti-B (group O), successive passing through the two medium supports is necessary.

One of the additional characteristics of IgG concentrates available on the market is their polyreactivity. It is to be recalled that polyclonal antibodies such as IgGs are normally combined with a single epitope (antigenic motif) in unique fashion. However, this strict specificity of antibodies may sometimes extend to other antigenic motifs and show affinity for secondary epitopes with weaker binding however than for the nominal motif. Polyclonal IgGs may react to a greater or lesser extent with structures such as actin, myosin, trinitrophenyl-modified albumin.

In this respect, intravenous immunoglobulins (IgIV) are preparations of polyclonal human IgGs containing:
 immune antibodies directed against external antigens and resulting from an immunization process;
 natural antibodies recognizing intracellular proteins, surface membrane antigens, circulating self proteins and the variable region of other antibodies. The latter are called anti-idiotype antibodies (Kazatchkine M. D. et al, Immunol. Rev., 139, 1994, 79-107).

Natural antibodies do not result from deliberate immunization (Coutinho A. et al, Curr. Opin. Immunol., 7, 1995, 812-818. They are polyreactive in that they express variable affinities for the self antigens (Berneman A. et al, Eur. J. Immunol., 22, 1992, 625-631 and Lacroix-Desmazes et al, J. Immunol. Methods, 216, 1988, 117-137).

Chemical treatments (6M urea, 1.3M sodium thiocyanate and acid treatment pH=2.0) of IgIVs can increase the polyreactive activity of these polyclonal immunoglobulins (Bouvet J. P. et al, J. Autoimmun., 16(2), 2001, 163-172). However, no beneficial effect has ever been demonstrated in patients treated with said immunoglobulins.

To summarize, the polyreactive activity of the antibodies present in an IgIV preparation can be due to:
 the presence of natural antibodies contained in each individual plasma,
 the presence of anti-idiotype antibodies contained in each individual plasma,
 the polyreactivity of the antibodies generated by the production method.

Therefore, some authors consider that polyreactivity is an intrinsic property of IgGs which are therefore naturally present in the human body.

Others demonstrate that a method to purify monoclonal or polyclonal IgGs can reveal polyreactivity that is undetectable before purification. Indeed methods to produce IgGs from plasma also generate a polyreactivity which translates as oxidative "stress" and partial carbonylation of IgGs during production.

This is confirmed by Bouvet J. P et al, Journal of Autoimmunity, 16, 2001, pp. 163-172, for whom polyclonal IgGs become highly polyreactive after treatment with urea in particular. It is also indicated in this document that part of the efficacy of IgGs in clinical use is attributed to their polyreactivity.

It follows that the polyreactivity of these IgG concentrates can therefore be explained by the combined presence of natural polyreactive IgGs and of polyreactive IgGs obtained by usual purification methods and accounting for 0.5 to 1% of all polyvalent IgGs. The treatment of patients with IgG preparations may require the administering of high doses of up to 1 to 2 g/kg. These dosages lead to short-term treatment e.g. in one day with quantities 7 to 10 times greater than the receiver's physiological IgG quantities. As a result, this level of polyreactive IgGs generated by the production method in IgG concentrates may cause adverse side effects such as fever, nausea or headache.

Therefore a distinction must be made between the polyreactivity of antibodies due to natural and anti-idiotype antibodies which, as shown by the Applicant in its patent application EP 1 059 088 has advantages, from the polyreactivity of the antibodies generated by the production method. It has been shown by the Applicant in patent application EP 1 059 088 that fractions of polyreactive IgGs naturally contained in the plasma, isolated from human polyvalent IgIVs, can advantageously be used to treat certain inflammatory diseases such as rheumatoid polyarthritis on account of the smaller dosage required for this fraction.

Therefore, to avoid adverse reactions both regarding haemolysis of red blood cells and regarding side reactions which may occur with massive administering of IgGs during a course of treatment, there appears to be a need for IgG concentrates for therapeutic use, in particular for intravenous injection, significantly depleted of anti-A and anti-B antibodies and whose polyreactivity generated by the production method is preferably largely reduced compared with IgG concentrates currently available on the market, whilst having at least identical efficacy with respect to immunotherapy.

Therefore, the invention concerns a concentrate of immunoglobulins G for therapeutic use, characterized in that its respective contents of anti-A and anti-B antibodies give a negative result with indirect Coombs test in vitro.

The invention also relates to a method to produce immunoglobulins G, with which it is possible not to generate these polyreactive antibodies which may be less well tolerated than natural and anti-idiotype antibodies. On this account, the IgIVs obtained with the method have a lower polyreactivity than the other tested IgIVs.

Under the invention, the IgGs of these concentrates are advantageously polyclonal IgGs obtained from blood plasma or from a blood plasma fraction already enriched with IgGs. The IgG concentrates for therapeutic use have IgG concentrations that are frequently used at present, preferably between 50 and 100 g/l. These concentrates are intended for clinical use, and may in particular be injected by intravenous route. For this purpose, they must be virally safe, and may optionally contain excipients such as stabilizers compatible with this clinical use.

The Applicant has found that it is possible to provide said IgG concentrates having anti-A and anti-B antibody contents that are much lower than those found in standard IgG concentrates i.e. those obtained by ethanol fractionation and/or using purification techniques associating chromatographies, as mentioned above, and which have not undergone additional treatment to remove the antibodies under consideration. Also their contents are well below the thresholds accepted by the European Pharmacopeia, which very significantly limits the risks of haemolysis in some patients receiving treatment. When the IgG concentrates of the invention are subjected to tests intended to evaluate the quantities of anti-A and anti-B antibodies, it is observed that the results of in vitro agglutination tests of A, B and/or AB red blood cells in the presence of anti-human IgG antibodies are systematically negative, notably at the initial concentration of 30 g/l laid down by the method of the European Pharmacopeia. The conducting of the indirect Coombs test, defined previously, with IgG concentrates of the invention therefore leads to systematically negative results even with IgG samples as such i.e. non-diluted. It would therefore appear that content of these anti-A and anti-B antibodies in these concentrates is already non-detectable by the ICT test.

If the level of anti-A and anti-B antibodies is very low in the IgG concentrates, the IAT test can no longer be applied, even more so under the conditions of the European Pharmacopeia since the agglutination reactions of the red blood cells no longer take place, even with the addition of anti-human IgG antibodies, since the density of anti-A and anti-B antibodies is too weak to allow bridges to be set up between the red blood cells by bonding of anti-A and anti-B antibodies fixed to the red blood cells and the anti-human IgG antibodies.

It is possible however to verify the presence of these anti-A and/or anti-B antibodies in very low concentration by causing immunohaemolysis of the red blood cells which fixed these antibodies and by measuring depletion compared with a conventional concentrate which has not undergone treatment to remove anti-A and anti-B antibodies. Immmunohaemolysis is a specific immunological reaction which occurs when the antibody is attached to its target in the presence of complement factors. Activation of complement activity leads to the release of performs which pierce the membrane of the red blood cell, allowing the haemoglobin to escape. All that is required subsequently is to use a sensitive method e.g. with radioactive tracers (see below) to measure the quantity of released haemoglobin, proportional to the quantity of anti-A and anti-B antibodies present.

The Applicant has demonstrated in particularly advantageous manner that the IgG concentrate of the invention has a content of anti-A antibodies of no more than 23 ng/mg IgG, in particular between 19 and 23 ng/mg IgG, and a content of anti-B antibodies of no more than 20 ng/mg IgG, in particular between 12 and 20 ng/mg IgG.

Advantageously, the Applicant has found that it is also possible to provide said IgG concentrates with a very low content of polyreactive IgGs, in particular those generated by the production method, thereby imparting a near non-polyreactive character to these concentrates which are just as efficient for the treatment of immunotherapies as the prior art IgG concentrates. This notable absence in these IgGs of a polyreactivity character due to the production method substantially reduces the risks of side effects which may arise subsequent to treatments requiring high dosages.

It is also advantageously possible to correct adverse effects arising from the presence of polyreactive IgGs in the IgG concentrate due to the production method, this presence generated in particular by oxidative "stress" and carbonylation during purification methods.

Preferably, the residual content of polyreactive IgGs is comprised between 0.01% and 0.1%, in particular between 0.07 and 0.1%. Under the invention, by content of polyreactive IgGs is meant a molar or weight percentage. This content is determined using methods described by the Applicant in patent application to 1 059 088.

The IgG concentrates of the invention are therefore defined by a notable absence of anti-A and anti-B antibodies in the active ingredients, which are directed against the epitopes present on the red blood cells.

The IgG concentrates may be in liquid or lyophilised form, in the presence of suitable stabilizers, and may be stored for later use. These stabilizers are advantageously those developed by the Applicant in its patent application WO 2004/091656 A2, namely a mixture of a sugar alcohol, preferably mannitol, sorbitol or their isomers, of glycine and of a non-ionic detergent such as Tween® 80, Tween® 20, Triton® X100 or Pluronic® F68, all three compounds being pharmaceutically acceptable.

The concentrations of the formulation were determined by the Applicant to stabilize liquid and/or lyophilised forms.

Preferably, the final mannitol concentrations in the concentrates lie between 30 g/l and 50 g/l, that of the detergent between 20 and 50 ppm, and that of glycine between 7 g/l and 10 g/l. The concentrations of these compounds represent the final concentrations in the IgG concentrates.

Said IgG concentrates, for therapeutic use, may in particular be injected via intravenous route as indicated previously. For this purpose, the IgG concentrates of the invention must be virally safe using a conventional solvent-detergent treatment for example known in the prior art, e.g. using a mixture of Tween® 80/TnBP or Triton® X 100/TnBP, and/or filtering steps for optional removal of viruses and/or other macromolecules which may not have been removed by the solvent-detergent viricide treatment e.g. the prion—the agent responsible for transmissible spongiform encephalopathy.

The invention also concerns a method to obtain an IgG concentrate such as mentioned above, comprising the following steps:

a) preparing an IgG concentrate by ethanol fractionation and/or chromatographic separation, associating a viral inactivation step, b) immunoaffinity chromatography by percolating said IgG concentrate through a mixture of medium supports whose matrixes are grafted with oligosaccharide groups which have antigenic similarity with blood groups A and B, and c) filtering to remove viruses and/or particles of a size greater than 20 nm.

It was found in remarkable manner by the Applicant that not only can this method advantageously be implemented on an industrial sale, but also that by combining the steps leading to the preparation of IgG concentrates with a specific step to remove anti-A and anti-B antibodies, it is possible to obtain an IgG concentrate of the invention, for therapeutic use, which also preferably comprises a content of polyreactive IgGs that is less than 0.1% relative to the total IgG content. Additionally, in said concentrate the content of undesired anti-A and anti-B antibodies is well below the lower limit of the test described in the European Pharmacopeia, even giving a negative result for the ICT test on said non-diluted samples.

Preferably, step a) of the method may itself be a method to obtain IgG concentrates such as those previously mentioned. It concerns ethanol fractionation developed by Cohn et al or chromatographic separation such as described for example in EP 0 703 922 and WO 99/64462. Particular preference is given to the methods developed by the Applicant in patent applications WO 94/29334 and WO 02/092632 A1, and more particularly to that described in WO 02/092632 A1. In this case, step a) of the method of the invention comprises pre-purification by precipitation of lipid contaminants from blood plasma or from an IgG-enriched fraction of blood plasma, single chromatography on an anion exchange resin conducted at alkaline pH, selective elution of the IgGs in one step using a suitable buffer at a pH comprised between 4 and 7.

Step a) of the method comprises viral inactivation treatment, preferably using a solvent-detergent as described by Horowitz in U.S. Pat. No. 4,764,369. This is judiciously carried out before a, or when applicable, before the subsequent chromatographic step performed in particular to remove the chemical residues of this treatment.

The collected IgG fraction is already sufficiently concentrated, and can then undergo additional concentration steps by ultrafiltration and sterilizing filtration.

This concentrate is then subjected to immunoaffinity chromatography on a mixture of two medium supports grafted with antigen groups having similarity with blood groups A and B, preferably on a column loaded with said medium mixture.

Preferably, the chromatographic medium consists of a natural crosslinked polymer matrix, of agarose type, on which spacers or coupling arms are grafted, which in turn are grafted with oligosaccharides these advantageously being trisaccharides corresponding to the epitopes of blood groups A and B. In particular, very good results are obtained using said medium whose trisaccharides, corresponding to the epitope of blood group A, have the structure N-acetylgalactosamine (GalNAc)-Galactose (Gal)-Fucose (Fuc), and those corresponding to the epitope of blood group B have the structure Galactose-Galactose-Fucose. Said medium is highly advantageously a gel or resin commercially available under the trade name GLYCOSORB ABO® from Glycorex Transplantation AS (Sweden).

By way of example, if this medium is used, the trisaccharide corresponding to the epitope of blood group A has the following structure:

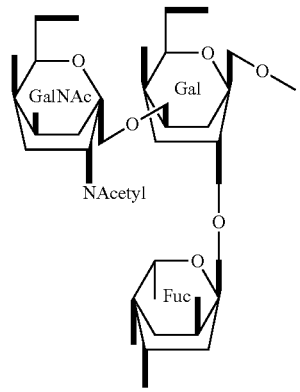

= —CH$_2$—CH$_2$—OH

= —CH$_2$—OH

= —CH$_3$

O = —O—

N-acetylgalactosamine (GalNAc)
Galactose (Gal)
Fucose (Fuc)

For example, if this medium is used, the trisaccharide corresponding to the epitope of blood group B has the following structure:

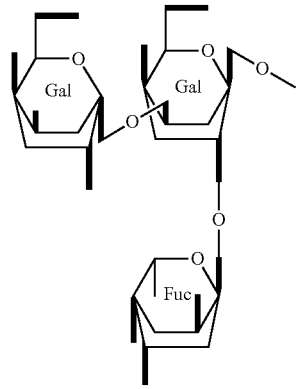

= —CH$_2$—CH$_2$—OH

= —CH$_2$—OH

= —CH$_3$

O = —O—

Advantageously, the medium mixture grafted with antigen groups similar to blood group A and blood group B has a respective proportion comprised between 25/75 and 75/25 (v/v). It is effectively possible to adjust the proportion of the two medium supports in the column to the donor population according to the distribution of its blood groups. For usual use, the column is preferably loaded with a 50/50 (v/v) mixture of each specific medium mentioned above. Analysis columns 15 to 25 cm in length can be used and 0.5 to 1 cm in diameter. For application on a pilot scale, columns with a length of 40 to 60 cm and width of 40 to 60 mm can be used. In this case it is possible to load the column with 600 ml of immunoaffinity medium.

Said medium is stored in IM NaOH between two cycles of use. Before use, it is washed with water.

The immunoaffinity chromatography column is then loaded with IgG concentrate, preferably to a proportion of 0.2 to 4 liters, in particular 1 to 2 liters, per milliliter of medium. The specificity of said medium does not require prior packing of the IgG fraction i.e. any IgG fraction or concentrate obtained by plasma fractionating techniques known in the prior art is suitable.

Percolation of the concentrate does not entail any eluting mechanism. Therefore, irrespective of the manner in which the IgG concentrate is obtained, it is percolated through the column, optionally using a pump. This percolation allows retention of the anti-A and anti-B antibodies and of the polyreactive IgGs. Advantageously, the column is then washed with water to collect the IgGs still present in the dead volume of the column.

After percolating the IgG concentrate, an IgG fraction is obtained depleted of anti-A and anti-B antibodies and of polyreactive IgGs derived from the production method. The anti-A and anti-B antibodies are retained on their antigenic motif of the chromatographic medium which modifies their conformation. Therefore the polyreactive IgGs generated during the production method are also retained on the sites exposed by this conformational change. The affinity of these polyreactive IgGs retained secondarily is much lower than that of the anti-A and anti-B antibodies. Their elution is possible by fractionation, after passing the IgGs, through the use of an elution buffer containing for example an alkaline-earth metal salt for having a concentration of between 0.1 and 1.5 M at a pH of 3-8, 6.

After step b), the method may comprise concentration steps by ultrafiltration and sterilizing filtration.

The chromatographic column and the medium are then washed with an acid solution such as glycine-HCl, pH 2.8, for desorption of the anti-A and anti-B antibodies retained on the medium. This medium is then rinsed with water and treated with a 1 M NaOH solution.

The IgG concentrate highly depleted of anti-A and anti-B antibodies and of polyreactive IgGs is then subjected to filtration to remove any viruses which may have resisted the solvent-detergent treatment and/or to remove other particles of size greater than 20 nm such as prions, IgG polymers generated during production steps, micelle lipopolysaccharides, aggregated nucleic acids and proteins. Said treatment is advantageously a nanofiltration implemented with filters of decreasing porosity from 100 to 15 nm, in particular three filters arranged in series and with decreasing retention thresholds of 100, 50 and 20 nm.

After step c), the method may comprise an additional step to add stabilizers firstly to ensure the stability of the IgG concentrates during their storage, and secondly to allow lyophilisation to prevent denaturing of the IgGs in the various phases associated therewith. Preferably, a single stabilizing formulation is added, that is pharmaceutically acceptable, meeting the objective of stabilizing the two envisaged storage forms of the IgGs i.e. liquid form or lyophilised form, and of maintaining and even improving the therapeutic efficacy of these IgGs as described in patent application WO 2004/091656 A2.

According to other embodiments, selective collection of other immunoglobulins is also possible, as described in patent WO 02/092632 A1.

The IgG concentrates are optionally subjected to a subsequent concentration step by ultrafiltration, followed by sterilizing filtration, and can be stored in bottles preferably at temperatures in the region of 4° C.

As largely explained above, the IgG concentrates of the invention have anti-A ant-B antibody contents that are well below the thresholds accepted by the European Pharmacopeia. Therefore, assay method 2.6.20 (1997) described therein may prove to be insufficiently sensitive to detect the antibodies under consideration present at very low levels in the IgG concentrates of the invention. It is therefore essential to develop assay methods for these antibodies requiring a lower detection threshold than that of the ICT test in the European Pharmacopeia applied to the detection of anti-A and anti-B antibodies.

Said assay method for anti-A and/or anti-B antibodies in the IgG concentrates of the invention comprises the steps consisting of:

a) preparing and calibrating a suspension of red cells of blood groups A, B and/or O Rhesus+, b) preparing solutions of monoclonal anti-D antibodies over a range of concentrations from 0 to 200 ng/ml in a biologically acceptable buffer, c) contacting said red blood cells with samples of IgG solutions or with the solutions of monoclonal anti-D antibodies, and incubating the mixtures of red blood cells thus obtained for a predetermined time, d) adding to each red blood cell mixture a fragment of anti-human IgG antibody F(ab')2 labelled with a fluorochrome, and incubating said red blood cells, e) subjecting each mixture of red blood cells obtained at step d) to flow cytometry, f) determining the content of anti-A and/or anti-B antibodies in the IgG concentrates.

One embodiment of said method to determine the content of anti-A and/or anti-B antibodies may comprise the preparation of a 1% v/v suspension of red cells of blood group A, B and/or 0 in a PBS buffer, of pH between 7.0 and 7.4, containing 0.8 to 1.5 wt. % of bovine serum albumin BSA. The red blood cells of the suspension are counted in a usual flow cytometry device, whose functioning is known to those skilled in the art, then the suspension is calibrated to 37 to 43.106 red corpuscles/ml of suspension.

Solutions of monoclonal anti-D antibodies are prepared, whose concentrations range from 0 to 200 ng/ml buffer, preferably a PBS buffer of pH between 7.0 and 7.4, optionally containing 0.8 to 1.5 wt. % bovine serum albumin BSA. Each solution thus prepared is assayed by absorptiometry to determine its molar extinction coefficient ($\epsilon$).

The IgG concentrates of the invention are then adjusted to a concentration in the range of values of from 1 to 5 mg/ml, preferably 1 mg/ml, using a PBS buffer of pH between 7.0 and 7.4, containing 0.8 to 1.5 wt. % bovine serum albumin BSA.

A volume of 50 to 100 µl of the suspension of red cells of each blood group is placed in each well of a microplate, e.g. a 96-well microplate, followed by 50 to 100 µl of IgG solution in this suspension of red blood cells, or 50 to 100 µl of anti-D antibody solutions in this suspension of red blood cells.

The whole is left to incubate for a time comprised between 1 h 30 and 2 h 30, in particular for 2 h at temperatures usually lying between 30 and 40° C., preferably 37° C.

The different mixtures of red blood cells thus obtained are then preferably washed with the PBS buffer containing the preceding BSA, and are centrifuged; then, to each mixture of red blood cells contained in a microwell plate, 50 to 100 µl F(ab'2) goat anti-human IgG antibody are added labelled with a fluorochrome e.g. phycoerythrin, present in the previously defined PBS and BSA buffer.

The whole is left to incubate for around 20 to 30 minute in the dark.

The different mixtures of red blood cells thus obtained are then washed and subjected to flow cytometry using any suitable apparatus available on the market containing a device to detect fluorescence of the analyzed compounds.

The mean fluorescence intensity (MFI) is given in relation to the concentration of monoclonal anti-D antibodies, and the linear regression equation is obtained using Excel software. Then, for each sample, the concentration in anti-D antibody equivalent is obtained using the linear regression equation. Since triple batches of the samples were assayed, the mean concentration is determined and the coefficient of variation is calculated using Excel software.

The content of anti-A and anti-B antibodies in the IgG concentrates of the invention can be deduced therefrom, which is advantageously the content given above.

Preferably, one assay method for the anti-A and anti-B antibodies in the above IgG concentrates is conducted by flow cytometry adapted to the context of the invention, whose principle is based on the use of human red cells of blood group A or B, according to the desired specific determination of anti-A and anti-B antibody content, using detection of a fluorescence signal proportional to the content of these antibodies.

Said assay method comprises the steps consisting of:
a) preparing and calibrating a suspension of red cells of blood group A or B,
b) contacting said red blood cells with diluted samples of IgG solutions, and incubating the mixture obtained for a pre-determined time,
c) incubating said red blood cells in the presence of an anti-IgG antibody labelled with a fluorochrome, and
d) subjecting the suspension of red blood cells obtained at step c) to flow cytometry.

A 1% (v/v) suspension of red cells is prepared of blood group A or B in a PBS buffer, of pH between 7.0 and 7.4, containing 0.8 to 1.5 wt. % of bovine serum albumin BSA. The red blood cells of the suspension are counted in a usual flow cytometry device, whose functioning is known to those skilled in the art, and the suspension is calibrated at 37 to 43.106 red blood cells/ml of suspension.

A volume of 50 to 100 µl of suspension is placed in each well of a 96-well microplate, followed by 50 to 100 µl of different IgG solutions diluted by increments of two by two from a solution of 30 g/l until an IgG solution of 0.234 g/l is obtained.

The whole is left to incubate for between 1 h 30 and 2 h 30, in particular 2 h, at a temperature usually ranging from 30 to 40° C., preferably 37° C.

The red blood cells are then washed with the PBS buffer containing the preceding BSA, and are centrifuged, then to each well 50 to 100 µl of $F(ab')_2$ goat anti-human IgG antibody is added, labelled with a fluorochrome such as phycoerythrin.

The whole (step c)) is incubated for around 20-30 min. away from light.

The suspension obtained is then washed and subjected to flow cytometry using any suitable apparatus available on the market comprising a fluorescence detection device for the analyzed compounds.

For example, the contents of anti-A and anti-B antibodies of three IgG concentrates called B1, B2 and B3, respectively prepared by ethanol fractionation following Cohn's method (cited above) (B1), according to patent application WO 02/092632 (B2) and according to patent application WO 02/092632 followed by immunoaffinity chromatography (B3) for depletion in anti-A and anti-B antibodies, and are indicated in Table 1 below. The results are given relative to the control titre of anti-A and anti-B antibodies in sample B1 whose content of these antibodies was arbitrarily set at 1 as reference.

TABLE 1

| Samples | Anti-A antibody titre | Anti-B antibody titre |
|---------|----------------------|----------------------|
| B1 | 1 | 1 |
| B2 | 3.65 | 3.85 |
| B3 | 0.68 | 0.52 |

The results in this table show firstly that the contents of anti-A and anti-B antibodies of the IgG concentrates (B1) prepared following Cohn's method, contain around four times less thereof than IgG concentrates (B2) prepared following the method described in WO 02/092632. In addition, the subsequent treatment of these IgG concentrates on specific immunoaffinity columns reduces the titre of anti-A antibodies by a factor close to 5, and of anti-B antibodies by a factor close to 7 (B3).

Another method to determine the content of anti-A and anti-B antibodies which can advantageously be applied, consists of in vitro lysis with the complement, known to those skilled in the art, but which has been specifically designed for the needs of the invention.

Said assay method comprises the steps consisting of:
a) radio-labelling a suspension of papain-treated red blood cells chosen from among the blood groups A, B, AB and O, previously counted, using a suitable radioactive marker,
b) contacting the radiolabelled red blood cells with samples of a predetermined volume of IgG concentrates,
c) adding an identical volume to the volume in step b) of normal serum of blood group AB,
d) incubating the mixture obtained at step c) for a pre-determined time, and
e) measuring the radioactivity of the incubated solution obtained.

A 1% (v/v) suspension of papain-treated red blood cells is prepared of blood group A, B, AB or 0, which is then counted in a Malassez cell to obtain 106 red blood cells. 100 µCi of $^{51}Cr$ (1 volume per 1 volume of red blood cells) are added. The whole is incubated for between 1 and 2 hours, and the radiolabelled red blood cells are then washed between 4 and 6 times.

The radiolabelled red blood cells are then contacted with samples of IgG concentrates at a concentration of preferably between 1 and 3 mg/ml, in particular 1.2 mg/ml per 4-6.106 radiolabelled red blood cells, in a volume of 100 µl for example.

An identical volume to the preceding volume, e.g. 100 µl of normal serum from blood group AB is then added to the preceding mixture to provide the different complement factors.

The reaction mixture obtained is then incubated, preferably for a time comprised between 3 and 5 h, in particular 4 h, at a temperature usually comprised between 30 and 40° C., preferably 37° C.

The reaction mixture is then preferably centrifuged, and the radioactivity of the incubated solution is measured using suitable, commercially available devices. The measured radioactivity of the solution is proportional to the extent of haemolysis of the treated red blood cells, and therefore to the content of anti-A and anti-B antibodies.

By way of example, the extent of haemolysis obtained for the red cells of blood groups A, B and AB, considering an IgG concentrate of the invention (B3) and an IgG concentrate of the prior art (C1) having the lowest haemolysis levels amongst all concentrates available on the market, are indicated in following Table 2.

TABLE 2

| % haemolysis of red blood cells | B3 | C1 (prior art) |
|---|---|---|
| Group A | 6 | 13 |
| Group B | 5 | 11 |
| Group AB | 6 | 13 |

The following examples illustrate embodiments of the present invention, without limiting its scope however.

EXAMPLE 1

A 40 g/l sample of IgG concentrate (B2) is obtained following the method described in WO 02/092632.

A chromatography column 50 cm in length and 44 mm in diameter is loaded with a 50/50 (v/v) mixture of GLY-COSORB ABO® medium grafted with trisaccharides corresponding to epitopes of blood group A and blood group B, and is then subjected to a prior washing step with 1200 ml water.

The B2 IgG concentrate is injected to the proportion of 0.2 l/ml of medium using a pump. Once this volume has percolated through the column, the column is washed with a minimum volume of water for an injectable preparation (IP) to collect the IgGs present in the dead volume of the column.

A B3 IgG concentrate is collected at around 40 g/l depleted of anti-A and anti-B antibodies and of polyreactive IgGs, which is then subjected to ultrafiltration to bring the concentrate to 60 g/l and to nanofiltration to remove viruses on three filters arranged in series and having decreasing retention thresholds of 100, 50 and 20 nm.

The stabilizing excipients consisting of a mixture of glycine (7 g/l), mannitol (30 g/l) and 20 ppm Tween 80® are dissolved in the IgG concentrate at 60 g/l and the IgG concentration is adjusted to 50 g/l using PI water, then the concentrate is subjected to sterile filtration and divided into bottles.

EXAMPLE 2

Quantification of Anti-A/Bs in IgIVs

1) Principle of the Assay 1-1) Preparation of Human Red Blood Cells

The suspensions of human red cells of blood group A Rhesus+, B Rhesus+ or O Rhesus+ are normalized to a concentration of $40 \times 10^6$ red blood cells/ml in PBS buffer+1% BSA at pH=7.4.

1-2) Preparation of the Monoclonal Anti-D Range

A preparation of monoclonal anti-D (called R297) is assayed for Optical Density (OD) at 280 nm against its PBS buffer of pH 7.4. The molar extinction coefficient (E) of the protein is calculated relative to its composition in different amino acids, and the concentration (C) in monoclonal anti-D is obtained by applying the formula:

C=OD/El in which I=width of the vessel to conduct OD measurement.

A range of 0 to 200 ng/ml of monoclonal anti-D antibodies is produced at 12 points (200; 150; 100; 75; 50; 25; 12.5; 6.25; 3.13; 1.56; 0.78 and 0 ng/ml).

1-3) Preparation of Immunoglobulin Solutions

Different intravenous immunoglobulins available on the market were tested. The chief characteristics of these immunoglobulins are detailed in the table below:

| Name | Supplier | Concentration |
|---|---|---|
| Polyvalent immunoglobulin | A | 50 g/l |
| Polyvalent immunoglobulin | B | 50 g/l |
| 10% intravenous human immunoglobulin | C | 100 g/l |
| IgNG 2 (*) | LFB | 50 g/l |
| IgNG 1 (**) | LFB | 50 g/l |
| TEGELINE ® | LFB | 50 g/l |

(*) obtained following the method described in WO 02/092632 followed by the immunoaffinity step described in Example 1.
(**) obtained following the method described in WO 02/092632 without the immunoaffinity step described in Example 1.

The different immunoglobulin preparations are adjusted to a concentration of 1 mg/ml using a PBS+1% BSA buffer with a pH of 7.4.

1-4) Sensitization of Red Blood Cells

In a round-bottomed microplate the following are deposited in the wells:

50 µl of the suspension of A Rhesus+, B Rhesus+ or 0 Rhesus+ red blood cells, with $40 \times 10^6$ red blood cells/ml, 50 µl of the anti-D range or 50 µl of the (IgIV) samples to be assayed.

The samples to be assayed are deposited in triple batches.

The plates are then incubated 2 hours at 37° C. under stirring.

1-5) Washings

The plates are centrifuged 1 minute at 770 g. The supernatant is discarded by inverting, then 200 µl of PBS+1% BSA is added to each well. The operation is repeated 3 times.

1-6) Addition of Conjugate and Washings

A goat anti-human IgG F(ab'2) (Fc specific) labelled with phycoerythrin (PE) (Beckmann Coulter, Ref: PN IM0550) is diluted to $\frac{1}{20}^{th}$ in PBS+1% BSA buffer, pH 7.4, then 50 µl of the solution are deposited in each well. The plate is then incubated 20 to 30 minutes at room temperature in the dark. Three successive washings are carried out as described under paragraph 1-5).

1-7) Flow Cytometry Reading

The suspensions of red blood cells are read off the flow cytometer (Beckmann Coulter FC500) using a suitable programme. Reading is conducted on 50 000 events, and the apparatus automatically calculates the mean fluorescence intensity (MFI) of each dot or sample.

1-8) Interpretation of Results

The MFI is obtained in relation to the concentration of monoclonal anti-D antibody, and the linear regression equation is obtained using Excel software. Then, for each sample, the concentration in equivalent anti-D antibodies is obtained using the linear regression equation. Since the samples were assayed in triple, the mean concentration is determined and the coefficient of variation (CV) is calculated using Excel software.

2) Results 2-1) Concentration in Anti-A Antibodies

| Name | Rhesus+ O red blood cells | Rhesus+ A red blood cells (anti-A Ig ng/mg Ig) | CV % |
|---|---|---|---|
| Polyvalent immunoglobulin A | ns | 55.4 | 4.5 |
| Polyvalent immunoglobulin B | ns | 44.4 | 3.4 |
| 10% intravenous human immunoglobulin, C | ns | 117.9 | 14.6 |
| IgNG 2 | ns | 22.2 | 5.5 |
| IgNG 1 | ns | 119.8 | 4.9 |
| TEGELINE | ns | 35.6 | 5.0 | ns = not significant 2-2) Concentration in Anti-B Antibodies

| Name | Rhesus+ O red blood cells | Rhesus+ B red blood cells (anti-B Ig ng/mg Ig) | CV % |
|---|---|---|---|
| Polyvalent immunoglobulin A | ns | 64.0 | 0.9 |
| Polyvalent immunoglobulin B | ns | 42.4 | 5.1 |
| 10% intravenous human immunoglobulin, C | ns | 89.0 | 20.5 |
| IgNG 2 | ns | 16 | 9.9 |
| IgNG 1 | ns | 155.2 | 4.8 |
| TEGELINE | ns | 44.2 | 8.0 | ns = not significant

3) Conclusions

The affinity step truly contributes towards the removal of anti-A and anti-B antibodies. Amongst the different immunoglobulins tested that are available on the market, product IgNG2 is the product which contains the least number of anti-A and anti-B antibodies.

EXAMPLE 3

A 1% (v/v) suspension of red cells of blood group A is prepared in PBS buffer, pH 7.4 containing 1 wt. % bovine serum albumin (BSA). 50 µl of the suspension of red blood cells is taken and added to a flow cytometer tube (Beckmann-Coulter Epics XL)) together with 50 µl of an internal labelling solution measuring the flow. The suspension is calibrated at 40·10$^6$ red blood cells/ml.

Eight batches of IgG solutions are prepared by successive dilution by factor 2 of the IgG concentrate (v/v) (B3) obtained in example 1, the most concentrated batch having 30 g/l, the most diluted having 0.234 g/l. A volume of 50 µl of the suspension is then placed in each well of a 96-well microplate, followed by 50 µl of the different diluted IgG solutions.

The whole is left to incubate for 2 h at a temperature of 37° C. under stirring.

Each well is then washed with 200 µl of PBS buffer containing the preceding BSA, and the microplate is centrifuged for 1 minute at 2000 rpm. After removing the supernatant, 50 µl of a solution of goat anti-human IgG F(ab'2) antibodies diluted to 1/20 with PBS-BSA are added, labelled with phyco-erythrin fluorochrome (Beckmann Coulter).

The whole is left to incubate for 30 min in the dark.

The suspension obtained is then washed as previously.

The residue of each well is dissolved in 100 µl of PBS-BSA. The volume contained in each well of the microplate is transferred to a tube in which 500 µl of Isoflow sheath fluid is added (Coulter) and then subjected to flow cytometry on Coulter-Beckmann Epics XL apparatus comprising software for data acquisition and analysis of results. Fluorometry is measured for each sample.

The same procedure is carried out for red cells of blood group B.

This operating mode is followed for three different batches of IgG (B3) and is also applied to three different batches of IgG prepared by ethanol fractionation according to Cohn's method (cited above) (B1).

The results obtained are given in Table 3 below:

TABLE 3

| Samples | Titre of anti-A antibodies | Titre of anti-B antibodies |
|---|---|---|
| B1 | 1 | 1 |
| B2 (3 batches) | 3.80; 3.55; 3.59 | 3.80; 4.45; 3.31 |
| B3 (3 batches) | 0.66; 0.68; 0.69 | 0.33; 0.73; 0.50 |

EXAMPLE 4

A 1% (v/v) suspension of papain-treated red cells of blood groups A, B, AB or O is prepared and counted in a Malassez cell to obtain 10$^6$ red blood cells. 100 µCi of $^{51}$Cr are added (1 volume per 1 volume of red blood cells). The whole is left to incubate for 1 hour, and the radiolabelled red blood cells are then washed 5 times.

The radiolabelled red blood cells are then contacted with samples of IgG concentrates (B2) obtained in example 1, at a concentration of 1.2 mg/ml per 5.106 radiolabelled red blood cells, in a volume of 100 µl.

An identical volume to the above of 100 µl normal serum from blood group AB is then added to the previous mixture to provide the different complement factors.

The reaction mixture obtained is then incubated 4 h at a temperature of 37° C.

The reaction mixture is then centrifuged for 1 minute at 2000 rpm and the radioactivity of the incubated supernatant solution is measured, using suitable devices available on the market. The measured radioactivity of the solution is proportional to the extent of haemolysis of the treated red blood cells, and consequently to the content of anti-A and anti-B antibodies.

Identical procedure is followed with red cells of blood groups B, AB and O, all being Rhesus+, and with a sample of serum from group O+. This operating mode is followed with three different batches of IgG (B2).

In addition, the procedure is applied to three batches of commercial samples of IgG concentrates, denoted C2 to C4, and a sample of serum from group O+ denoted C5 included as negative control.

The measured radioactivity of the solution is proportional to the extent of haemolysis of the treated red blood cells, and consequently to the quantity of anti-A and anti-B antibodies bound to the red blood cells.

The haemolysis results are given in Table 4 below:

TABLE 4

| % haemolysis of red blood cells | B3 | C2 | C3 | C4 | C5 |
|---|---|---|---|---|---|
| Group A+ | 6 | 16 | 13 | 30 | 34 |
|  | 6.2 | 15.5 | 13.5 | 31 | 34.4 |
|  | 6.5 | 16.3 | 13.2 | 31 | 34.6 |
| Group B+ | 5 | 13.1 | 11.2 | 25 | 34 |
|  | 4.8 | 13.3 | 10.8 | 25.3 | 34.4 |
|  | 5.4 | 13.4 | 10.9 | 25.4 | 34.6 |
| Group AB+ | 6 | 16 | 15.1 | 31 | 34 |
|  | 5.9 | 15.7 | 15.1 | 31.4 | 34.4 |
|  | 6.5 | 16.3 | 15.4 | 30.9 | 34.6 |
| Group O+ | 0.1 | 0.2 | 0.22 | 0.33 | 2 |
|  | 0.15 | 0.25 | 0.24 | 0.32 | 2.2 |
|  | 0.12 | 0.21 | 0.24 | 0.30 | 2.7 |

The results obtained show that the IgG concentrate B3, which was subjected to affinity chromatography according to the invention, contains the lowest quantity of anti-A and anti-B antibodies, since the haemolysis percentages of the red blood cells originating from the different blood groups are the lowest.

No haemolysis is observed with the red blood cells of phenotype O+ included as negative control.

EXAMPLE 5

Measurement of the polyreactivity of IgG concentrates B2 (before immunoaffinity chromatography) and after this chromatography (IgG concentrate B3) described in example 1.

The measurement of the polyreactivity of these IgG concentrates is conducted following patent EP 1 059 088 using two antigens which react with polyreactive IgGs. These are myosin and albumin modified by dinitrophenyl groups (DNP Albumin).

Table 5 gives the enrichment factors of the polyreactive IgGs in samples B2, B3 and C4 of example 3 whose IgG content was arbitrarily set at 1 as reference.

These measurements were conducted on three different batches of the IgG concentrates under consideration.

TABLE 5

| Sample | Myosin | DNP Albumin |
|---|---|---|
| B1 | 1 | 1 |
| B2 (3 batches) | 1.2; 0.8; 1.2 | 3.2; 1.0; 2.0 |
| B3 (3 batches) | 0.4; 0.4; 0.4 | 1.0; 1.0; 1.0 |
| C4 (3 batches) | 2.0; 2.0; 2.0 | 8.0; 6.0; 7.0 |

The results indicate that the B3 IgG concentrate of the invention contains 5 to 8 times fewer polyreactive IgGS than the prior art concentrate C4.

EXAMPLE 6

Example comparing the efficacy of the B3 IgG concentrates depleted of anti-A and anti-B antibodies and of polyreactive IgGs, with the B1 IgG concentrates The test included mice deficient in FcγRI and FcγRIII receptors treated with a view to evaluating the immunomodulating activity of the IgG concentrates of the invention. These animals were used as model for thrombocytopenic purpura.

As control an IgG concentrate (B1) was used, obtained by ethanol fractionation according to Cohn.

The experimental protocol was the protocol described by Teeling J. L. et al (Blood, 15 Aug. 2001, vol. 98, number 4, pp. 1095-1099).

The platelets, destroyed by injection of anti-platelet monoclonal IgGs from $9·10^8$/ml to $2·10^8$/ml, rose to $7·10^8$/ml in those animals treated with IgG concentrates B1 and B3 at a therapeutic dose of 1 g/kg.

The immunomodulating activity of the B3 IgG concentrate according to the invention was not modified by the immunoaffinity chromatography.

The invention claimed is:

1. A therapeutic concentrate of polyclonal immunoglobulins G (IgG), wherein the respective contents of anti-A and anti-B antibodies conforms to a negative result for the Coombs in vitro indirect test, in particular a content of anti-A antibodies of no more than 23 ng/mg IgG, and a content of anti-B antibodies of no more than 20 ng/mg IgG, and wherein the residual content of polyreactive IgGs of between 0.01% and 0.1% relative to the total IgG content.

2. The therapeutic concentrate according to claim 1, further containing stabilizers intended to allow the storage of said concentrate.

3. The therapeutic concentrate according to claim 2, wherein the stabilizers are a mixture of a sugar alcohol, of glycine and of a non-ionic detergent.

4. The therapeutic concentrate according to claim 1 that can be injected via intravenous route.

5. Method to obtain an IgG concentrate according to claim 1, comprising the steps of:
   a) preparing an IgG concentrate from plasma by ethanol fractionation and/or chromatographic separation, associating a viral inactivation step,
   b) immunoaffinity chromatography by percolation of said IgG concentrate on a mixture of media whose matrices are grafted with oligosaccharide groups having antigenic similarity with blood groups A and B, and
   c) filtration to remove viruses and/or particles of size greater than 20 nm step (d) collecting and concentrating the IgG.

6. Method according to claim 5, wherein step a) of the method of the invention comprises pre-purification by precipitation of lipid contaminants from said blood plasma or from an IgG-enriched fraction of said blood plasma, single chromatography on an anion exchange resin conducted at alkaline pH and selective elution of the IgGs in one step using a suitable buffer of pH between 4 and 7.

7. Method according to claim 5 or 6, wherein the oligosaccharide groups having antigenic similarity with blood groups A and B are trisaccharides corresponding to epitopes of blood groups A and B.

8. Method according to claim 7, wherein the trisaccharides corresponding to the epitope of blood group A have the structure N-acetyl-galactosamine (GalNAc)—Galactose (Gal)—Fucose (Fuc), and those corresponding to the epitope of blood group B have the structure Galactose-Galactose-Fucose.

9. Method according to claims 5 to 8, wherein the viral inactivation step is conducted with a solvent-detergent.

10. Method according to claims 5 to 9, comprising the steps of concentration by ultrafiltration, and sterilizing filtration.

11. Method according to claims 5-9 and 10, wherein filtration to remove viruses is conducted by nanofiltration.

12. Method according to claims 5-9 and 10 which, after step c) comprises a step to add stabilizers for the storage of said IgG concentrate.

* * * * *